United States Patent
Joung et al.

(10) Patent No.: US 9,403,111 B2
(45) Date of Patent: Aug. 2, 2016

(54) METHOD FOR STERILIZING WATER TREATMENT APPARATUS HAVING PLURALITY OF TANKS

(75) Inventors: Jin-Kyu Joung, Seoul (KR); Ki-Chul Kim, Seoul (KR); You-Shin Kim, Seoul (KR)

(73) Assignee: Coway Co., Ltd (KR)

( * ) Notice: Subject to any disclaimer, the term of this patent is extended or adjusted under 35 U.S.C. 154(b) by 348 days.

(21) Appl. No.: 14/119,134

(22) PCT Filed: May 24, 2012

(86) PCT No.: PCT/KR2012/004115
§ 371 (c)(1),
(2), (4) Date: Nov. 20, 2013

(87) PCT Pub. No.: WO2012/165806
PCT Pub. Date: Dec. 6, 2012

(65) Prior Publication Data
US 2014/0096799 A1    Apr. 10, 2014

(30) Foreign Application Priority Data

May 31, 2011  (KR) .................. 10-2011-0052195
Jul. 25, 2011  (KR) .................. 10-2011-0073507
May 15, 2012  (KR) .................. 10-2012-0051326

(51) Int. Cl.
| | | |
|---|---|---|
| B08B 9/00 | (2006.01) | |
| B01D 35/16 | (2006.01) | |
| A61L 2/03 | (2006.01) | |
| A61L 2/24 | (2006.01) | |
| C02F 1/461 | (2006.01) | |
| C02F 1/50 | (2006.01) | |

(52) U.S. Cl.
CPC ................. *B01D 35/16* (2013.01); *A61L 2/035* (2013.01); *A61L 2/24* (2013.01); *A61L 2202/23* (2013.01); *C02F 1/461* (2013.01); *C02F 1/50* (2013.01); *C02F 2303/14* (2013.01)

(58) Field of Classification Search
None
See application file for complete search history.

(56) References Cited

U.S. PATENT DOCUMENTS

2005/0115883 A1    6/2005    Takemoto et al.

FOREIGN PATENT DOCUMENTS

| KR | 1020020071311 | 9/2002 |
|---|---|---|
| KR | 1020050074004 | 7/2005 |
| KR | 1020060056079 | 5/2006 |
| KR | 1020090128785 | 12/2009 |
| KR | 1020100128661 | 12/2010 |

OTHER PUBLICATIONS

PCT/ISA/237 Written Opinion issued on PCT/KR2012/004115 (pp. 5), mailed Nov. 23, 2012.

*Primary Examiner* — Eric Golightly
(74) *Attorney, Agent, or Firm* — The Farrell Law Firm, P.C.

(57) ABSTRACT

Provided is a method for sterilizing a water treatment apparatus having a plurality of tanks. The method includes, performing a sterilization preparation process to drain purified water from the first tank until a first amount of purified water is left, performing a sterilizing process to sterilize the first tank by supplying the sterilized water supplied from the sterilizing module, to drain water from the first tank through a first water outlet pipe until a second amount of water is left in the first tank, and to drain the second amount of water remaining in the first tank into the second tank through a second water outlet pipe.

15 Claims, 6 Drawing Sheets

METHOD FOR STERILIZING WATER TREATMENT APPARATUS HAVING PLURALITY OF TANKS

PRIORITY

This application is a National Phase Entry of PCT International Application No. PCT/KR2012/004115 filed May 24, 2012, and claims priority to Korean Patent Application Nos. 10-2011-0052195, 10-2011-0073507 and 10-2012-0051326 filed with the Korean Intellectual Property Office on May 31, 2011, Jul. 25, 2011 and May 15, 2012, respectively, the content of each of which is incorporated herein by reference.

TECHNICAL FIELD

The present invention relates to a method for sterilizing a water treatment apparatus having a plurality of tanks, and more particularly, to a method for sterilizing tanks and flow passages of a water treatment apparatus having a plurality of tanks.

BACKGROUND ART

In general, water purifiers may be classified into ultra filtration (UF) membrane water purifiers and reverse osmosis (RO) membrane water purifiers, depending on a water purifying method carried out thereby.

Among them, the RO membrane water purifier has been known as being superior to other water purifying schemes in terms of removing pollutants.

The RO membrane water purifier may include a filtering unit including a sediment filter that receives raw water from a faucet and removes dust particles, dregs, various suspended bodies, and the like therefrom, through 5-micron fine filters; a pre-carbon filter that removes carcinogens (e.g., trihalomethane (THM)), synthetic detergents, harmful chemicals (e.g., insecticides), residual chlorine components, and the like, by activated carbon adsorption; an RO membrane filter that includes a 0.0001-micron RO membrane, removes heavy metals (e.g., lead and arsenic), sodium, various germs, and the like, and discharges concentrated water through a drain pipe; and a post-carbon filter that removes unpleasant odors, tastes, and colors contained in water having passed through the RO membrane filter.

The UF membrane water purifier uses a UF membrane filter instead of an RO membrane filter. The UF membrane filter is a porous filter having tens to hundreds of nanometer (nm) pores, which removes pollutants in water through numerous fine pores that are distributed on a membrane surface.

As described above, the RO membrane water purifier or the UF membrane water purifier may use four filters. However, the RO membrane water purifier or the UF membrane water purifier may additionally use an antibacterial filter or a functional filter. Moreover, the RO membrane water purifier or the UF membrane water purifier may be used as a combinational filter having functions of a variety of filters. For example, a function of a sediment filter and a function of a pre-carbon filter may be embodied in a single combinational filter.

However, in such a water purifier, a post-carbon filter or the like may be easily polluted by bacteria, and bacteria may flow into a storage tank in water. Therefore, bacteria may proliferate in the storage tank. In addition, external bacteria or microorganisms may pass through purified water stored in the storage tank and proliferate therein, and water scale may be formed on the inner wall of the storage tank.

In order to sterilize bacteria or microorganisms having proliferated in a storage tank, there is proposed a technology that sterilizes a storage tank and a purified water drainage passage by adding separate sterilizing chemicals thereto.

However, this method of supplying sterilizing chemicals may be burdensome and inefficient in terms of sterilization management because a user or a water purifier manager needs to separately perform a sterilizing chemical supply operation. That is, in the case of supplying sterilizing chemicals, a user needs to periodically insert sterilizing chemicals when an automatic injection of sterilizing chemicals is impossible. Also, even in the case that automatic injection of sterilizing chemicals is possible, a user also needs to periodically insert sterilizing chemicals. Therefore, this method is very inconvenient to a user.

Furthermore, in the case of injecting sterilizing chemicals, a concentration of the sterilizing chemicals may be unnecessarily high. In some cases, a user or a manager may inject a large amount of sterilizing chemicals or a small amount of sterilizing chemicals. Therefore, sterilizing chemicals may remain in a water purifier after a cleaning process. Therefore, after the cleaning process, it is necessary to perform a rinsing process several times. If the rinsing process is not adequately performed, the remaining sterilizing chemicals may cause harm to a user' health, and a user may experience unpleasant odors from the sterilizing chemicals.

Moreover, since the water purifier manager needs to perform the sterilizing chemical supply operation, costs for sterilizing the water purifier may be incurred. Thus, the user may feel burdened by service charges.

In particular, the water purifier is not sterilized or cleaned by itself. In most cases, the water purifier is sterilized or cleaned by a service agent. Therefore, it is very inconvenient to a user, and the reliability of the water purifier may be degraded over time.

Conditions in which sterilizing chemicals dissolve or flow out from a tank may also be different depending on a water purifier operation condition (for example, a raw water pressure, a flow rate, or the like). For example, when a flow rate is low, a sterilizing concentration may be relatively high. On the contrary, when a flow rate is high, a sterilizing concentration may be low. Therefore, it is very difficult to control the sterilization. When a concentration of sterilizing chemicals is high, unpleasant odors may be generated.

Since the main sterilizing material used in sterilizing chemicals is OCl—, either having a low pH or a very high pH, a lot of odor may be generated thereby. Also, sterilizing performance is merely 1/70 of that of HOCl. Therefore, a large amount of OCl— sterilizing material as compared to HOCl may be required for sterilizing a tank having the same capacity. As will later be described, sterilizing performance may be significantly degraded as compared to a case of using an electrolyzer to produce a sterilizing material mainly made of HOCl, containing a mixed oxidant (MO).

In order to solve a problem of a water purifier which is sterilized using such sterilizing chemicals, there has been proposed a method of automatically sterilizing a storage tank using an electrolyzer. FIG. 1 illustrates a water treatment apparatus disclosed in Korean Patent Application Publication No. 2009-0128785.

As illustrated in FIG. 1, a conventional water treatment apparatus 10 filters raw water, supplied from a raw water supply unit such as a water main 15, through a water purifying filter 14, stores the filtered water in a storage tank 13, and supplies the filtered water through a dispenser 17 when a user requests the supply of water. In this case, if pollution of purified water stored in the storage tank 13 is detected by a pollution level sensor 13a provided in the storage tank 13, or a predetermined period of time has elapsed, hypochlorous acid may be generated using a chloride supply device 11 and an electrolysis device 12, and be supplied to the storage tank 13. A process of cleaning the storage tank 13, which is disclosed in Korean Patent Application No. 2009-0128785, will be described below in detail.

When it is necessary to clean the storage tank 13 through the pollution level sensor 13a, water stored in the storage tank 13 is completely drained into sewage 16 using an extraction pipe G and the dispenser 17 or through a drain pipe F. Alternatively, most water stored in the storage tank 13 is drained into a low water level or a position near a floor. When the drainage of water stored in the storage tank 13 is completed, a valve Vg or Vf is shut off. In order to supply chlorides, such as NaCl or KCl, from the chloride supply device 11 to the electrolysis device 12, and generate a chloride aqueous solution, raw water (service water) may be supplied through a raw water supply pipe B, without passing through the water purifying filter 14, or purified water filtered by the water purifying filter 14 may be supplied through a raw water supply pipe C disposed at a rear end of the water purifying filter 14. In this case, when the chloride and raw water (service water) or purified water is supplied to the electrolysis device 12 and a sufficient period of time has elapsed to dissolve the chloride, an aqueous solution containing hypochlorous acid is generated through the electrolysis (oxidation-reduction reaction) of the chloride aqueous solution by applying a voltage to electrodes 12a of the electrolysis device 12. The storage tank 13 is fully filled with the generated hypochlorous acid aqueous solution and is maintained during a predetermined period time necessary to sterilize and clean the storage tank 13. After the predetermined period of time has elapsed, the hypochlorous acid aqueous solution is drained from the storage tank 13. In order to remove the hypochlorous acid aqueous solution, water having passed through the water purifying filter 14 is supplied to the storage tank 13 through the purified water supply pipe D up to a level of the storage tank 13 equal to that when full, or service water which has not passed through the water purifying filter 14 is supplied to the storage tank 13 through a rinse pipe H up to a full water level of the storage tank 13. After a predetermined period of time has elapsed, a rinse process of draining rinse water stored in the storage tank 13 is performed several times. In this way, the process of cleaning the storage tank 13 is completed. Then, raw water is filtered through the water purifying filter 14, and purified water is supplied to the storage tank 13, so that a user can use the purified water.

Since the conventional water treatment apparatus is provided with a single storage tank 13, it is easy to sterilize and clean the storage tank. However, since a water treatment apparatus having an ice maker and a plurality of tanks has recently been introduced, there is a need for a sterilizing method that takes into consideration water flow among a plurality of tanks.

DISCLOSURE OF INVENTION

Technical Problem

An aspect of the present invention provides a method for sterilizing tanks and flow passages of a water treatment apparatus having a plurality of tanks.

Solution to Problem

According to an aspect of the present invention, there is provided a method for sterilizing a water treatment apparatus having a sterilizing module, which generates or receives sterilized water and supplies the sterilized water, a first tank, and a second tank, the method including: performing a sterilization preparation process to drain purified water from the first tank until a first amount of purified water is left in the first tank; performing a sterilizing process to sterilize the first tank by supplying the sterilized water supplied from the sterilizing module to the first tank, to drain water from the first tank through a first water outlet pipe until a second amount of water is left in the first tank, and to drain the second amount of water remaining in the first tank into the second tank through a second water outlet pipe; and performing a cleaning process to clean the first tank by supplying purified water to the first tank, and to drain the purified water used to clean the first tank into the second tank.

In the sterilizing process, water of the first tank may be drained into the second tank through the second water outlet pipe until a second amount of water is left in the first tank, and the second amount of water remaining in the first tank may be drained through the first water outlet pipe.

The first water outlet pipe may be configured to supply water to an intermediate device included in the water treatment apparatus, and the intermediate device may be connected to the second tank and configured to bypass water supplied from the first water outlet pipe to the second tank.

The intermediate device may be any one of a third tank, an ice maker, a carbonated water maker, and a syrup addition device.

The sterilization preparation process may include: supplying a preset volume of purified water to the first tank; and draining the purified water stored in the first tank during a first draining period, the first draining period being a period of time taken to drain an amount of water corresponding to a difference between the preset volume and the first amount of water.

The preset volume may be a maximum storage amount of the first tank.

The method may further include draining water stored in the second tank after the sterilization preparation process.

The sterilizing process may include: sterilizing the first tank by supplying a preset volume of the sterilized water supplied from the sterilizing module to the first tank; draining the sterilized water stored in the first tank through the first water outlet pipe during a second draining period; and draining the water remaining in the first tank through the second water outlet pipe, the second draining period being a period of time taken to drain an amount of water corresponding to a difference between the preset volume and the second amount of water.

The sterilizing process may include: sterilizing the first tank by supply a preset volume of the sterilized water supplied from the sterilizing module to the first tank; draining the sterilized water stored in the first tank through the second water outlet pipe during a second draining period; and draining the water remaining in the first tank through the first water outlet pipe, the second draining period being a period of time taken to drain an amount of water corresponding to a difference between the preset volume and the second amount of water.

The method may further include draining sterilized water stored in the second tank after the sterilizing process.

The cleaning process may include: cleaning the first tank by supplying a preset volume of purified water to the first tank; draining the supplied purified water stored in the first tank into the second tank; and draining the purified water drained into the second tank.

The purified water may be supplied to the first tank at the same time as the draining of the purified water drained into the second tank, or the purified water may be supplied to the first tank after the draining of the purified water drained into the second tank.

The first tank may include: a first water outlet pipe configured to transfer water stored in the first tank to an intermediate device included in the water treatment apparatus; a second water outlet pipe configured to transfer water stored in the first tank to the second tank; and a water intake pipe configured to drain water stored in the first tank to the outside. The first water outlet pipe, the water intake pipe, and the second water outlet pipe may be installed on the side of the first tank in order from top to bottom.

The second tank may include: a drain line configured to drain water stored in the second tank; a drain valve configured to open/close the drain line; and a drain pump installed in the drain line.

The first amount of water may be determined, depending on a target dilution level of the sterilized water.

When the second amount of water is stored in the first tank, a height of a water surface may fall to within a range between a height of the water intake pipe and a height of the first water outlet pipe.

The sterilizing module may generate the sterilized water by using one of an electrolytic sterilizer employing electrolysis and a chemical sterilizer employing sterilizing chemicals.

According to another aspect of the present invention, there is provided a method for sterilizing a water treatment apparatus having a sterilizing module, which generates or receives sterilized water and supplies the sterilized water, a first tank, a second tank, and an intermediate device, the method including: performing a sterilization preparation process to drain purified water from the first tank into the second tank until a first amount of purified water is left in the first tank, and to drain purified water from the second tank until a second amount of purified water is left in the second tank; performing a first sterilizing process to sterilize the first tank by supplying sterilized water supplied from the sterilizing module thereto, and to drain water from the first tank into the second tank until a third amount of water is left in the first tank; performing a second sterilizing process to drain sterilized water from the second tank into the intermediate device until a fourth amount of sterilized water is left in the second tank; performing a third sterilizing process to drain the second amount of water remaining in the first tank into the second tank; performing a fourth sterilizing process to drain the sterilized water stored in the second tank; and performing a cleaning process to clean the first tank by supplying purified water to the first tank, and to drain the purified water used to clean the first tank into the second tank.

In the sterilizing process, when water of the first tank is drained into the second tank until the third amount of water is left in the first tank during the first sterilizing process, the second amount of water remaining in the first tank is drained into the intermediate device during the third sterilizing process, and a fourth amount of the sterilized water stored in the second tank is drained into the intermediate device during the second sterilizing process.

In the sterilizing process, when water of the first tank is drained into the second tank until the third amount of water is left in the first tank during the first sterilizing process, the second amount of water remaining in the first tank may be drained into the intermediate device during the third sterilizing process, and a fourth amount of the sterilized water stored in the second tank may be drained into the intermediate device during the second sterilizing process.

When the first tank is sterilized by supplying the sterilized water supplied from the sterilizing module thereto, water of the first tank may be drained into the intermediate device until the third amount of water is left in the first tank, the second amount of water remaining in the first tank may be drained into the second tank, and a fourth amount of the sterilized water stored in the second tank may be drained into the intermediate device.

The method may further include a fourth sterilizing process to drain the sterilized water stored in the second tank after the third sterilizing process.

The intermediate device may be any one of a third tank, an ice maker, a carbonated water maker, and a syrup addition device.

The sterilization preparation process may include: draining water from the second tank; supplying a preset volume of purified water to the first tank; draining the purified water stored in the first tank into the second tank during a first draining period; and draining the purified water stored in the second tank during a second draining period. The first draining period may be a period of time taken to drain an amount of water corresponding to a difference between the preset volume and the first amount of water, and the second draining period may be a period of time taken to drain an amount of water corresponding to a result of a subtraction of the first amount of water and the second amount of water from the preset volume.

The first sterilizing process may include: sterilizing the first tank by supplying a preset volume of the sterilized water supplied from the sterilizing module to the first tank; and draining the sterilized water stored in the first tank into the second tank during a third draining period. The third draining period may be a period of time taken to drain an amount of water corresponding to a difference between the preset volume and the third amount of water.

In the second sterilizing process, the sterilized water may be drained from the second tank during a fourth draining period. The fourth draining period may be a period of time taken to drain the fourth amount of water from the second tank.

The cleaning process may include: cleaning the first tank by supplying a preset volume of purified water to the first tank; draining the supplied purified water stored in the first tank into the second tank; draining some of the purified water from the second tank into the intermediate device; and draining the rest of the purified water from the second tank.

The sterilizing module may generate the sterilized water by using one of an electrolytic sterilizer employing electrolysis and a chemical sterilizer employing sterilizing chemicals.

The preset volume may be a maximum storage amount of the first tank.

According to another aspect of the present invention, there is provided a method for sterilizing a water treatment apparatus having a sterilizing module, which generates or receives sterilized water and supplies the sterilized water, a first tank, a second tank, and an intermediate device, the method including: performing a sterilization preparation process to drain purified water from the first tank into the second tank until a first amount of purified water is left in the first tank, and to drain purified water from the second tank until a second amount of water is left in the second tank; performing a first sterilizing process to sterilize the first tank by supplying sterilized water supplied from the sterilizing module thereto, and to drain water from the first tank into the second tank until a third amount of water is left in the first tank; performing a second sterilizing process to drain sterilized water from the second tank into the intermediate device until a fourth amount of sterilized water is left in the second tank; performing a third sterilizing process to drain the second amount of water remaining in the first tank into the intermediate device; performing a first cleaning process to clean the first tank by supplying purified water to the first tank, to drain some of the purified water used to clean the first tank into the intermediate device, and to drain the rest of the purified water into the second tank; and performing a second cleaning process to drain some of the purified water from the second tank, and to drain the rest of the purified water from the second tank.

The intermediate device may be any one of a third tank, an ice maker, a carbonated water maker, and a syrup addition device.

The sterilization preparation process may include: draining water from the second tank; supplying a preset volume of purified water to the first tank; draining the purified water stored in the first tank into the second tank during a first draining period; and draining the purified water stored in the second tank during a second draining period. The first draining period may be a period of time taken to drain an amount of water corresponding to a difference between the preset volume and the first amount of water, and the second draining period may be a period of time taken to drain an amount of water corresponding to a result of a subtraction of the first amount of water and the second amount of water from the preset volume.

The first sterilizing process may include: sterilizing the first tank by supplying a preset volume of the sterilized water supplied from the sterilizing module to the first tank; and draining the sterilized water stored in the first tank into the second tank during a third draining period. The third draining period may be a period of time taken to drain an amount of water corresponding to a difference between the preset volume and the third amount of water.

In the second sterilizing process, the sterilized water may be drained from the second tank during a fourth draining period. The fourth draining period may be a period of time taken to drain the fourth amount of water from the second tank.

The first cleaning process may include: cleaning the first tank by supplying a preset volume of purified water to the first tank; draining some of the supplied purified water stored in the second tank into the intermediate device; and draining the rest of the purified water stored in the first tank into the second tank.

The second cleaning process may include: draining some of the purified water stored in the second tank into the intermediate device; and draining the rest of the purified water stored in the second tank.

The sterilizing module may generate the sterilized water by using one of an electrolytic sterilizer employing electrolysis and a chemical sterilizer employing sterilizing chemicals.

According to another aspect of the present invention, there is provided a method for sterilizing a water treatment apparatus having a sterilizing module, which generates or receives sterilized water and the sterilized water, a first tank, a second tank, and an intermediate device, the method including: performing a sterilization preparation process to drain purified water from the first tank until a first amount of purified water is left in the first tank; performing a sterilizing process to sterilize the first tank by supplying sterilized water supplied from the sterilizing module thereto, to drain water from the first tank into the second tank until a second amount of water is left in the first tank, and to drain the second amount of water remaining in the first tank into the intermediate device; and performing a cleaning process to clean the first tank by supplying purified water to the first tank, to drain some of the purified water used to clean the first tank into the second tank, and to drain the rest of the purified water into the intermediate device.

The intermediate device may be any one of a third tank, an ice maker, a carbonated water maker, and a syrup addition device.

The sterilization preparation process may include: supplying a preset volume of purified water to the first tank; and draining the purified water stored in the first tank into the second tank during a first draining period. The first draining period may be a period of time taken to drain an amount of water corresponding to a difference between the preset volume and the first amount of water.

The sterilizing process may include: sterilizing the first tank by supplying a preset volume of the sterilized water supplied from the sterilizing module to the first tank; draining the sterilized water stored in the first tank into the second tank during a second draining period, the second draining period being a period of time taken to drain an amount of water corresponding to a difference between the preset volume and the second amount of water; and draining water remaining in the first tank into the intermediate device.

The cleaning process may include: cleaning the first tank by supplying a preset volume of purified water to the first tank; draining some of the supplied purified water stored in the first tank into the second tank; draining the rest of the supplied purified water stored in the first tank into the intermediate device; and draining the purified water stored in the second tank.

The sterilizing module may generate the sterilized water by using one of an electrolytic sterilizer employing electrolysis and a chemical sterilizer employing sterilizing chemicals.

The preset volume may be a maximum storage amount of the first tank.

Advantageous Effects of Invention

According to exemplary embodiments of the present invention, a method for sterilizing a water treatment apparatus having a plurality of tanks may sterilize and clean a first tank and a second tank while preventing sterilized water from diffusing into a water intake pipe.

BRIEF DESCRIPTION OF DRAWINGS

The above and other aspects, features and other advantages of the present invention will be more clearly understood from the following detailed description taken in conjunction with the accompanying drawings, in which.

BEST MODE FOR CARRYING OUT THE INVENTION

Figure 1:
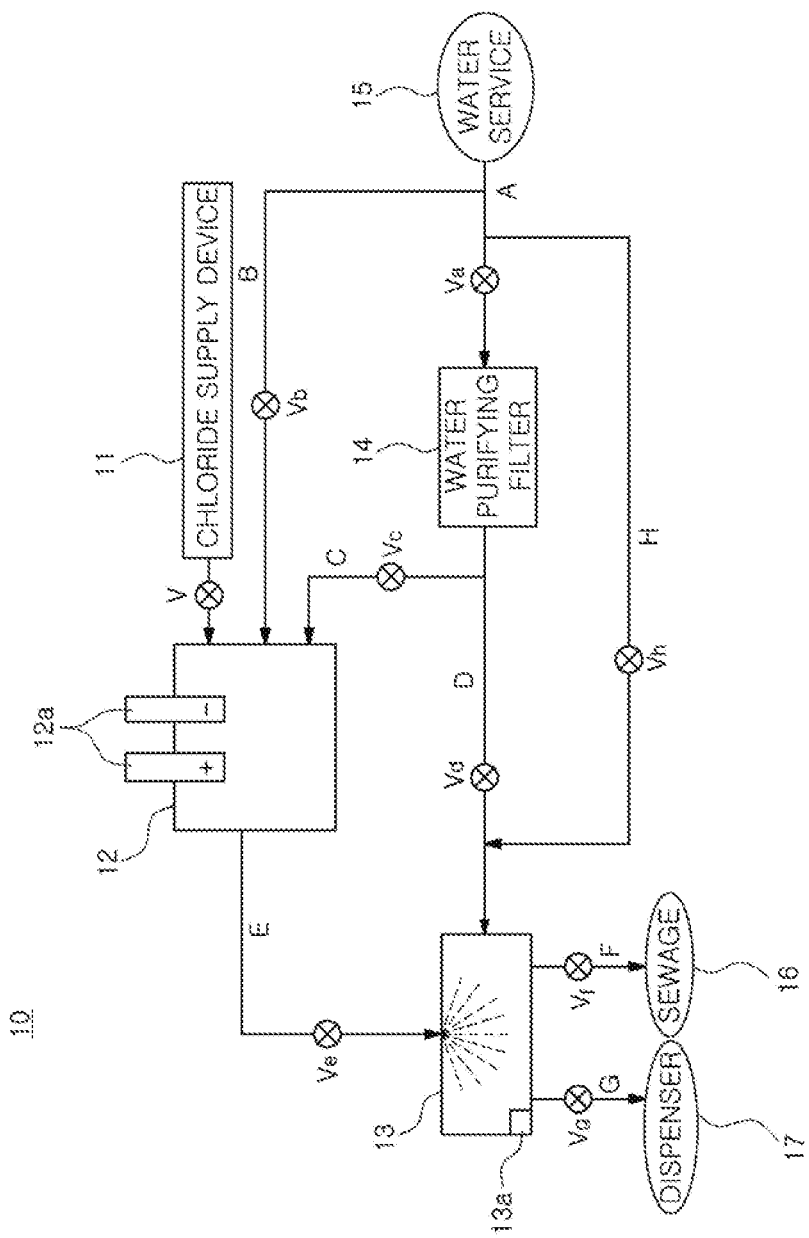
FIG. 1 is a block diagram schematically illustrating a configuration of a conventional water treatment apparatus.

Exemplary embodiments of the present invention will now be described in detail with reference to the accompanying drawings. However, in the description of the operational principles associated with the embodiments of the present invention, a detailed description of known art inventions or constructions is omitted because it may obscure the spirit of the present invention unnecessarily In order to clearly describe the exemplary embodiments of the present invention, parts unrelated to the present invention are omitted. The same or equivalent elements are referred to as the same reference numerals throughout the specification.

Unless explicitly described to the contrary, the terms "include" and "have" will be understood to imply the inclusion of stated elements but not the exclusion of any other elements.

Water treatment apparatuses may be used to treat water or wastewater and produce ultra-pure water, and may be used for various purposes such as industrial purposes and domestic purposes (including business purposes). However, the present invention particularly relates to water treatment apparatuses that are used to produce drinking water. Since water treatment apparatuses for producing drinking water receive raw water (or water), filter the raw water, and generate purified water for drinking, they will be referred to as water purifiers in a narrow sense. Such water purifiers may be configured to receive raw water (or water), filter the raw water with a filtering unit, and supply normal-temperature purified water to users, and may also be configured to heat or cool the normal-temperature purified water and supply hot water or cold water to users.

Among the water treatment apparatuses for producing drinking water, there are functional water generators that supply a variety of types of functional water, such as ionized water, carbonated water, and oxygenated water, as well as purified water. In addition, there are water heaters, water coolers, ice makers and the like that heat/cool/freeze water received from a water supply unit such as a water tank. In this specification, the term "water treatment apparatus" is used as a general term for a water purifier, a functional water generator, a water heater, a water cooler, an ice maker, and any apparatus having at least one of the functions thereof. Although typical water purifiers are exemplified for the convenience of description, such water purifiers should be understood merely as examples of water treatment apparatuses according to exemplary embodiments of the present invention.

In the following description, the water treatment apparatuses applicable to exemplary embodiments of the present invention relate to a reservoir type water treatment apparatus (water purifier) that may purify water supplied from a raw water supply unit by passing the supplied water through various filters, store the filtered purified water (hereinafter, simply referred to as "purified water") in a separate storage space, and drain the stored purified water to the outside.

Such water treatment apparatuses remove impurity particles, heavy metals, or other harmful chemicals from raw water, such as tap water or natural water, by filtering the raw water through filters of a filtration unit.

In addition, the water treatment apparatuses applicable to exemplary embodiments of the present invention may be configured to sterilize and clean tanks and sterilized water flow passages by generating or receiving sterilized water, supplying the sterilized water to the tanks, and draining the sterilized water.

In particular, the water treatment apparatuses applicable to exemplary embodiments of the present invention may be configured to sterilize and clean tanks and sterilized water flow passages by generating sterilized water containing a sterilizing material, such as mixed oxidant (MO), by performing electrolysis on only purified water, filtered while passing through at least some filters of a filtration unit, without adding separate "sterilizing chemicals" or "chlorides", and by supplying the sterilized water to the tanks and the flow passages. The term "electrolysis" as used herein includes an "oxidation-reduction reaction". In particular, the water treatment apparatuses applicable to exemplary embodiments of the present invention may be configured to generate sterilized water containing high-concentration MO by electrolyzing only purified water, without adding separate chlorides through a chloride supply device.

According to another exemplary embodiment, the water treatment apparatuses may be configured to sterilize and clean tanks and sterilized water flow passages by generating sterilized water by mixing chemicals and purified water, supplying the sterilized water to the tanks, and draining the sterilized water.

According to another exemplary embodiment, the water treatment apparatuses may be configured to sterilize and clean tanks and sterilized water flow passages by storing sterilized water generated or prepared in the outside, or receiving sterilized water when needed, and supplying the stored or received sterilized water to the tanks and the flow passages.

Figure 2:
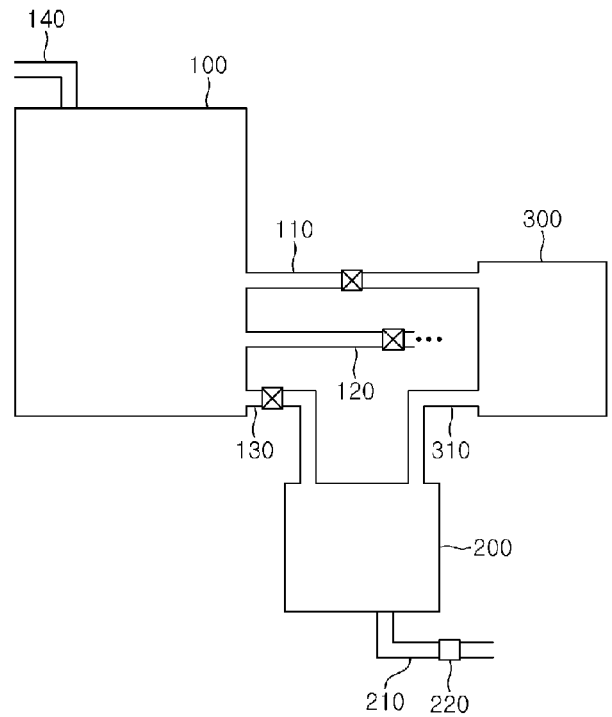
FIG. 2 is a schematic diagram illustrating a configuration of a water treatment apparatus having a plurality of tanks, to which a sterilizing method according to an exemplary embodiment of the present invention is applied.

FIG. 2 is a schematic diagram illustrating a configuration of a water treatment apparatus having a plurality of tanks, to which a sterilizing method according to an exemplary embodiment of the present invention is applied;

A first tank 100 stores purified water having passed through a filtration unit and selectively drains the purified water. The first tank 100 may store sterilized water supplied from a sterilizing module.

An intermediate device 300 processes the purified water supplied from the first tank 100. As illustrated in FIG. 2, the intermediate device 300 may provide a flow passage that bypasses fluid, such as the purified water or sterilized water supplied from the first tank 100, to a second tank 200. Specifically, the intermediate device 300 may be a third tank configured to store the purified water supplied from the first tank 100 and heat or cool the stored purified water, an ice maker configured to make ice by cooling the supplied purified water, or a carbonated water maker configured to make carbonated water by supplying carbon dioxide to the purified water. In addition, the intermediate device 300 may be a syrup addition device configured to add syrup or scent to the purified water. However, according to another exemplary embodiment of the present invention, the intermediate device 300 may not be included in the water treatment apparatus, depending on the purpose of the water treatment apparatus. In this case, the first tank 100 may include a separate flow passage that bypasses fluid, such as the supplied purified water or sterilized water, to the second tank 200, and may also include a flow passage that directly drains water from the first tank 100 to a drain pipe conduit.

Hereinafter, a water treatment apparatus including an ice maker as an example of the intermediate devices 300 will be described.

The ice maker 300 may receive purified water from the first tank 100 and make ice of the purified water. The ice maker 300 may employ an ice making method using an ice tray and an immersion evaporator, and may employ an injection type ice making method that makes ice by injecting water into a cooling container. Specifically, the water may be cooled using a thermoelectric module (TEM) or evaporation heat of a refrigerant liquefied by a compressor or the like. In addition, any ice making method or any cooling method may be employed as long as it can be applied to the water treatment apparatus.

The second tank 200 may receive purified water from the first tank 100 and ice from the ice maker 300 to make cold water, and store the cold water. That is, the second tank 200 may make cold water by mixing normal-temperature purified water and ice, and store the cold water. In the case in which the intermediate device 300 is not the ice maker, the second tank 200 may cool the stored purified water through a separate cooling device using a thermoelectric module or refrigerant gas.

The first tank 100 may be supplied with purified water or sterilized water through a water inlet pipe 140. Although not illustrated, sterilized water generated by an electrolytic sterilizer may be supplied through the water inlet pipe 140 in a sterilizing mode.

In addition, the first tank 100 may include a first water outlet pipe 110, a second water outlet pipe 130, and a water intake pipe 120.

The first water outlet pipe 110 may transfer water stored in the first tank 100 to the ice maker 300. The first water outlet pipe 110 may include a valve for controlling water flow. If necessary, water flow may be controlled using a water jet pump.

The second water outlet pipe 130 may transfer water stored in the first tank 100 to the second tank 200. The second water outlet pipe 130 may include a valve for controlling water flow. If necessary, water flow may be controlled using a water jet pump.

The water intake pipe 120 may drain water stored in the first tank 100 to the outside. In particular, the water intake pipe 120 may be connected to a purified water cock and transfer purified water to a user. In addition, if necessary, the water intake pipe 120 may include a valve for controlling the supply of purified water.

As illustrated in FIG. 2, the first water outlet pipe 110, the water intake pipe 120, and the second water outlet pipe 130 may be installed on the side of the first tank 100 in order from top to bottom. In practice, the first water outlet pipe 110, the second water outlet pipe 130, and the water intake pipe 120 are disposed on a bottom of the first tank 100 in order for effective arrangement of purification, and a height difference between the pipes may not be great. According to exemplary embodiments, the second water outlet pipe 130, the water intake pipe 120, and the first water outlet pipe 110 may be installed in order from top to bottom.

The ice maker 300 may further include a bypass passage 310 that can bypass supplied purified water to the second tank 200, without storing the supplied purified water in an ice tray. For example, the bypass passage 310 may serve as a passage through which ice is transferred from the ice tray to the second tank 200. The bypass passage 310 is used for a partial drainage of the sterilized water, as described below.

The second tank 200 may include a drain line 210, a drain valve (not illustrated), and a drain pump 220.

The drain line 210 is configured to drain water or sterilized water, stored in the second tank 200, as live water. The drain line 210 is provided as a drain pipe conduit connected to a bottom of the second tank 200.

The drain valve may control the opening/closing of the drain line 210, and the drain pump 220 may be installed in the drain line 210. The drain pump 220 is used to more effectively drain water stored in the second tank 200. Even in the case that the drain valve is opened, water is not drained rapidly if a cross-section of the drain line 210 is narrow. Since water is not drained completely, old purified water or sterilized water used in a sterilizing process may remain in the second tank 200.

Recent water treatment apparatuses have tended to reduce the entire size thereof, so as to allow them to be installed in an indoor space while supporting various functions. Therefore, there is a significant risk in reducing a cross-sectional area of the drain line 210. Even when the drain valve is opened, it is hard to drain water completely. Hence, the drain pump 220 may also be provided together with the drain valve.

In general, the drain pump 220 may be provided with a motor. The motor may be a DC motor capable of controlling an operating speed using an input voltage, or an AC motor capable of controlling an operating speed through a frequency regulation. In general, the drain valve may be provided with a latch valve.

Although not illustrated, an electrolytic sterilizer may be installed in the water inlet pipe 140. The electrolytic sterilizer may be configured to generate sterilized water, including a sterilizing material such as mixed oxidant (MO), through electrolysis using only purified water filtered by at least some of filters provided in the filtration unit.

The electrolytic sterilizer sterilizes or destroys microorganisms or bacteria remaining in water by passing water between electrodes of different polarities. In general, sterilization of purified water by electrolysis may be performed by a combination of a direct oxidation reaction that directly oxidizes microorganisms with a positive electrode, and an indirect oxidation reaction that oxidizes microorganisms with a variety of mixed oxidants (for example, residual chorine, ozone, OH radicals, and oxygen radicals) that may be generated at a positive electrode In addition, although not illustrated, a chemical sterilizer may be installed in the water inlet pipe 140. The chemical sterilizer may be configured to generate sterilized water, including a sterilizing material, using only purified water filtered by at least a part of filters provided in the filtration unit.

Furthermore, although not illustrated, a device configured to receive sterilized water from the outside may be installed in the water inlet pipe 140. The device may receive and store sterilized water prepared or generated on the outside, or may supply the sterilized water immediately to the water inlet pipe 140.

Hereinafter, a method for sterilizing the above-described water treatment apparatus having the plurality of tanks will be described.

Figure 3:
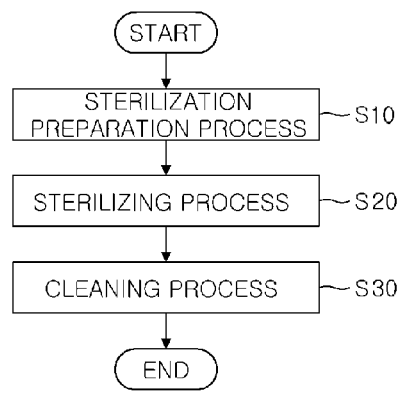
FIG. 3 is a flow diagram illustrating a method for sterilizing a water treatment apparatus having a plurality of tanks, according to an exemplary embodiment of the present invention.

FIG. 3 is a flow diagram illustrating a method for a water treatment apparatus having a plurality of tanks, according to an exemplary embodiment of the present invention.

In a sterilization preparation process S10, purified water may be drained until a first amount of purified water is left in the first tank 100. The first amount of the purified water may be determined, depending on a target dilution level of sterilized water being supplied at high concentration. If necessary, the first amount of the purified water may be determined to the extent that the sterilized water is prevented from diffusing into the water intake pipe 120.

In a sterilizing process S20, the first tank 100 may be sterilized by supplying sterilized water thereto. Water of the first tank 100 may be drained into the second tank 200 through the ice maker 300 until a second amount of water is left therein. The second amount of water remaining in the first tank 100 may be drained into the second tank 200. Alternatively, according to exemplary embodiments, after the second amount of water is drained into the second tank 200, water remaining in the first tank 100 may be drained into the second tank 200 through the ice maker 300.

That is, after the first tank 100 is sterilized by supplying sterilized water thereto, sterilized water may be divided and drained. This is undertaken to prevent sterilized water from diffusing into the water intake pipe 120. When the second amount of water is stored in the first tank 100, a height of a water surface may fall to within a range between a height of the water intake pipe 120 and a height of the first water outlet pipe 110.

That is, by draining upper sterilized water and lower sterilized water drained through different pipes, the diffusion of sterilized water into the water intake pipe 120 may be minimized. A detailed description thereof will be given below.

In a cleaning process S30, the first tank 100 may be cleaned by supplying purified water thereto. The purified water used to clean the first tank 100 may be drained into the second tank 200, and the second tank 200 may be cleaned with the purified water drained thereinto. Even in the case that the sterilized water is drained, the sterilized water may remain in several places in the first tank 100 and the second tank 200. In this case, the remaining sterilized water may be washed out by the purified water.

In addition, after the sterilization preparation process S10 and the sterilizing process S20, purified water and sterilized water remaining in the second tank 200 may be drained. Furthermore, when the cleaning process 30 is completed, purified water may be supplied to the first tank 100, so that a user can drink the purified water. This may be done after or during the draining of the purified water used to clean the second tank 200.

As described above, the method for sterilizing the water treatment apparatus may sterilize and clean the plurality of tanks while minimizing the diffusion of sterilized water into the water intake pipe 120.

Figure 4:
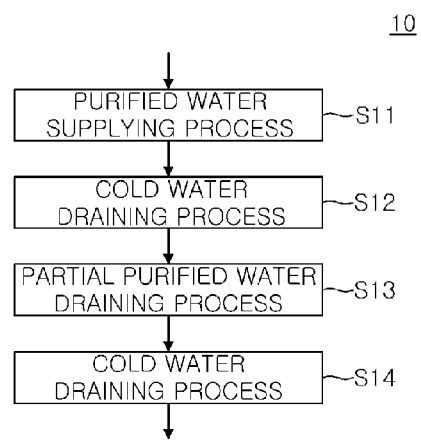
FIG. 4 is a flow diagram illustrating a detailed flow of a sterilization preparation process in the method for sterilizing the water treatment apparatus, according to an exemplary embodiment of the present invention.

FIG. 4 is a flow diagram illustrating a detailed flow of the sterilization preparation process in the method for sterilizing the water treatment apparatus, according to an exemplary embodiment of the present invention;

Referring to FIG. 4, the sterilization preparation process S10 according to an exemplary embodiment of the present invention may include a purified water supplying process S11, a cold water draining process S12, and a partial purified water draining process S13, and may further include a cold water draining process S14.

In the purified water supplying process S11, a preset volume of purified water may be supplied to the first tank 100. In the cold water draining process S12, cold water remaining in the second tank 200 may be drained. In the purified water supplying process S11, a preset volume of purified water may be supplied to the first tank 100 using a flowmeter, which may be provided in the water inlet pipe 140, or by a method of measuring a period of time during which purified water is supplied to the first tank 100. However, an amount of purified water remaining in the first tank 100 is difficult to measure unless an amount of purified water supplied or used is continuously tracked. Therefore, an amount of purified water remaining in the first tank 100 may be exactly determined by fully filling the first tank 100 with purified water. That is, the preset volume may be set to a maximum storage amount of the first tank 100.

In addition, when cold water remains in the second tank 200, a desired amount of purified water may not be drained from the first tank 100. Therefore, it is necessary to drain water completely from the second tank 200 in the cold water draining process S12.

In the partial purified water draining process S13, purified water from the first tank 100 may be drained into the second tank 200 during a first draining period. The first draining period may be a period of time taken until an amount of water corresponding to a difference between the preset volume and the first amount of water is drained from the first tank 100 to the second tank 200. On the other hand, as described above, when the preset volume is set to a maximum storage amount of the first tank 100, the first draining period may be a period of time taken until an amount of water corresponding to a difference between the maximum storage amount of the first tank 100 and the first amount of water is drained from the first tank 100 to the second tank 200. The first draining period may be determined by the maximum storage amount of the first tank 100, the first amount of water, an amount of drainage of the second water outlet pipe 130 per unit time, or the like, and may be previously determined in designing the water treatment apparatus. Therefore, the first draining period may be calculated theoretically or experimentally in designing the water treatment apparatus. That is, in the partial purified water draining process S13, purified water may be drained during the first draining period determined using an estimated amount of the remaining purified water (full water level through the supply of purified water), a drainage rate, and the first amount of water. Alternatively, in the partial purified water draining process S13, a flowmeter may be used. Specifically, a flowmeter may be provided in the water outlet pipe of the first tank 100. When an amount of water corresponding to a difference between the preset volume and the first amount of water is drained into the second tank 200, the drainage of water may be stopped. In this case, as compared to a case in which water is drained during the first period of time, an exact amount of purified water may be drained into the second tank 200.

In the cold water draining process S14, purified water drained from the first tank 100 may be drained from the second tank 200, such that the second tank 200 is ready to store water drained from the first tank 100 or the ice maker 300.

Figure 5:
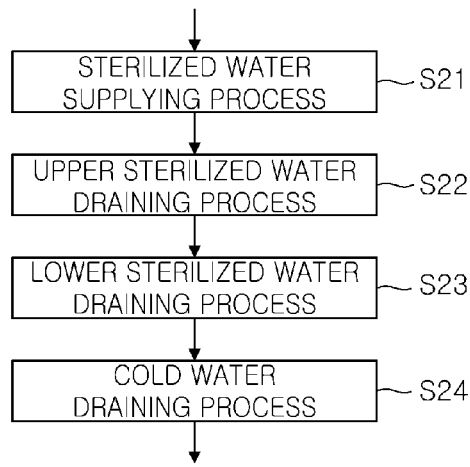
FIG. 5 is a flow diagram illustrating a detailed flow of a sterilizing procedure in the method for sterilizing the water treatment apparatus, according to an exemplary embodiment of the present invention.

FIG. 5 is a flow diagram illustrating a detailed flow of the sterilizing process in the method for sterilizing the water treatment apparatus, according to an exemplary embodiment of the present invention;

Referring to FIG. 5, the sterilizing process S20 according to an exemplary embodiment of the present invention may include a sterilized water supplying process S21, an upper sterilized water draining process S22, and a lower sterilized water draining process S23, and may further include a cold water draining process S24.

In the sterilized water supplying process S21, the first tank 100 may be supplied with sterilized water through a water inlet pipe 140. In addition, the supplied sterilized water may sterilize a lower portion of the first tank 100 while diffusing into the remaining purified water. However, it takes a time for the sterilized water to completely diffuse into the purified water. Therefore, if only the sterilized water is drained before the sterilized water completely diffuses into the lower portion of the first tank 1, the diffusion of the sterilized water into the water intake pipe 120 may be minimized.

As described above, when assuming that the first water outlet pipe 110, the water intake pipe 120, and the second water outlet pipe 130 are installed on the side of the first tank 100 in order from top to bottom, sterilized water stored in an upper portion of the first tank 100 may be drained into the ice maker 300 through the first water outlet pipe 110 in the upper sterilized water draining process S22. The sterilized water drained into the ice maker 300 may be transferred to the second tank 200 along the bypass passage 210 of the ice maker 300. That is, when the sterilized water is drained through the second water outlet pipe 130, high-concentration sterilized water may gradually move downward and flow directly into the water intake pipe 120. However, if sterilized water is drained into the ice maker 300 through the first water outlet pipe 110, sterilized water stored in a portion higher than the water intake pipe 120 is continuously drained. Therefore, the inflow of the sterilized water into the water intake pipe 120 may be minimized. In addition, since the lower portion of the first tank 100 may be sterilized with the diffused sterilized water, there is no problem in sterilizing the lower portion of the first tank 100. In order to drain only the upper sterilized water, the sterilized water may be drained into the ice maker 300 during a second draining period in the upper sterilized water draining process S22. The second draining period may be a period of time taken until an amount of water corresponding to a difference between the preset volume and a second amount of water is drained through the first water outlet pipe 110. As described above, in the second amount of water, a height of a water surface of the first tank 100 may fall to within a range between a height of the water intake pipe 120 and a height of the first water outlet pipe 110. The preset volume may be a maximum storage amount of the first tank 100. Therefore, the second draining period may be determined, considering the maximum storage amount of the first tank 100, the second amount of water, and an amount of drainage of the first water outlet pipe 110 per unit time.

A flowmeter may be directly provided in the first water outlet pipe 110 to adjust an amount of sterilized water that is drained from the first tank 100. That is, an amount of sterilized water drained from the first tank 100 may be measured using the flowmeter, and the drainage of water from the first tank 100 may be stopped when the measured amount of sterilized water is equal to a difference between the maximum storage amount of the first tank 100 and the second amount of water. In this case, although a separate flowmeter is required, an exact amount of sterilized water may be drained from the first tank 100, as compared to a case in which water is drained during the second draining period.

In the lower sterilized water draining process S23, the purified water remaining in the first tank 100 and the diffused sterilized water may be drained into the second tank 200 through the second water outlet pipe 130. Therefore, the lower portion of the first tank 100 may be sterilized, and the sterilized water may be completely drained.

In the cold water draining process S24, water stored in the second tank 200 may be drained, and the second tank 200 may be ready to receive water drained from the first tank 100.

According to exemplary embodiments, the second water outlet pipe 130, the water intake pipe 120, and the first water outlet pipe 110 may be installed on the side of the first tank 100 in order from top to bottom. In this case, in the sterilizing process 20, water may be directly drained into the second tank 200 through the second water outlet pipe 130. If the second amount of water is left in the first tank 100, water may be bypassed to the ice maker 300 through the first water outlet pipe 110. Therefore, in this case, the inflow of sterilized water into the water intake pipe 120 may be minimized.

Figure 6:
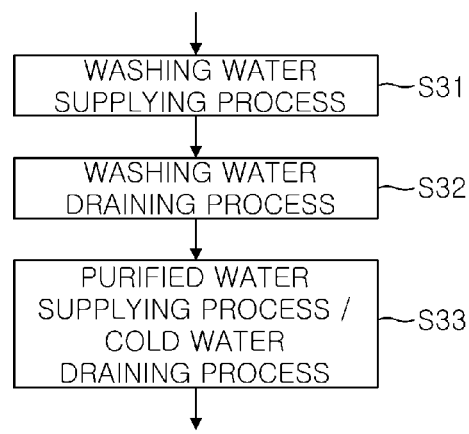
FIG. 6 is a flow diagram illustrating a detailed flow of a cleaning procedure in the method for sterilizing the water treatment apparatus, according to an exemplary embodiment of the present invention.

FIG. 6 is a flow diagram illustrating a detailed flow of the cleaning process in the method for sterilizing the water treatment apparatus, according to an exemplary embodiment of the present invention.

Referring to FIG. 6, the cleaning process S30 according to an exemplary embodiment of the present invention may include a washing water supplying process S31 and a washing water draining process S32, and may further include a cold water draining process S33. In addition, as described above, a purified water supplying process may be performed at the same time as the cold water draining process S33, or may be performed prior to the cold water draining process S33.

In the washing water supplying process S31, a preset volume of purified water may be supplied through the water inlet pipe 140, and the first tank 100 may be cleaned with the supplied purified water. The preset volume may be a maximum storage amount of the first tank 100 so as to clean the entirety of the first tank 100.

In the washing water draining process S32, purified water used to clean the first tank 100 may be drained into the second tank 200. That is, the first tank 100 is emptied so that purified water may be stored therein. In addition, the purified water drained into the second tank 200 may clean the second tank 200. If necessary, the first water outlet pipe 110 may be cleaned by draining some of the washing water into the ice maker 300.

Since the purified water supplying process and the cold water draining process S33 have been described above, a detailed description thereof will be omitted.

The above-described processes may prevent a problem in which sterilized water flows into the water intake pipe 120, and thus, a user drinks water containing sterilized water after the sterilizing and cleaning process. Furthermore, a plurality of tanks may be sterilized and cleaned.

Hereinafter, an example in which the sterilizing method is applied to a water treatment apparatus having a plurality of tanks will be described will be described.

A mode for sterilizing and cleaning the water treatment apparatus is driven by a user' input or in a preset period or time point.

In step 1, the first tank 100 is filled with purified water through the water inlet pipe 140 up to a full water level.

In step 2, water of the second tank 200 is completely drained, or is drained until 430 seconds have elapsed. 430 seconds are enough time to completely drain water from the second tank 200.

In step 3, water of the first tank 100 is drained into the second tank 200 for 110 seconds.

In step 4, water of the second tank 200 is completely drained, or is drained until 370 seconds have elapsed. 370 seconds are enough time to completely drain water from the second tank 200.

In step 5, the first tank 100 is filled with sterilized water through the water inlet pipe 140 up to a full water level.

In step 6, sterilized water of the first tank 100 is drained into the ice maker 300 through the first water outlet pipe 110 for 180 seconds.

In step 7, sterilized water of the first tank 100 is drained into the second tank 200 through the second water outlet pipe 130 for 70 seconds.

In step 8, water of the second tank 200 is completely drained, or is drained until 430 seconds have elapsed. 430 seconds are enough time to completely drain water of the second tank 200.

In step 9, the first tank 100 is filled with purified water through the water inlet pipe 140 up to a full water level.

In step 10, water of the first tank 100 is drained into the second tank 200 for 230 seconds.

In step 11, water of the second tank 200 is completely drained, or is drained until 430 seconds have elapsed. 430 seconds are enough time to completely drain water from the second tank 200.

A display device, such as an LED, may be used to indicate to the user that the sterilizing function is being executed. For example, an LED for sterilization indication may be turned on and off (ON for 3 seconds, OFF for 1 second), and a front LED may be dimmed as a whole.

In addition, the drain valve and the drain pump 220 installed in the second tank 200 may be operated with constant time difference, so as to prevent the drain valve from malfunctioning due to a drainage pressure of the drain pump 200.

When the intermediate device is operating, for example, when the ice maker 300 makes ice, the sterilizing process may be started after the operation of the intermediate device is completed, for example, after the ice making process is completed.

In addition, if purified water or sterilized water does not reach a full water level within a predetermined time, such a case may be recognized as an emergency situation, such as an interruption of a water supply, and the sterilizing operation may be restarted later. The water treatment apparatus may inform the user of the emergency situation through the display device.

Figure 7:
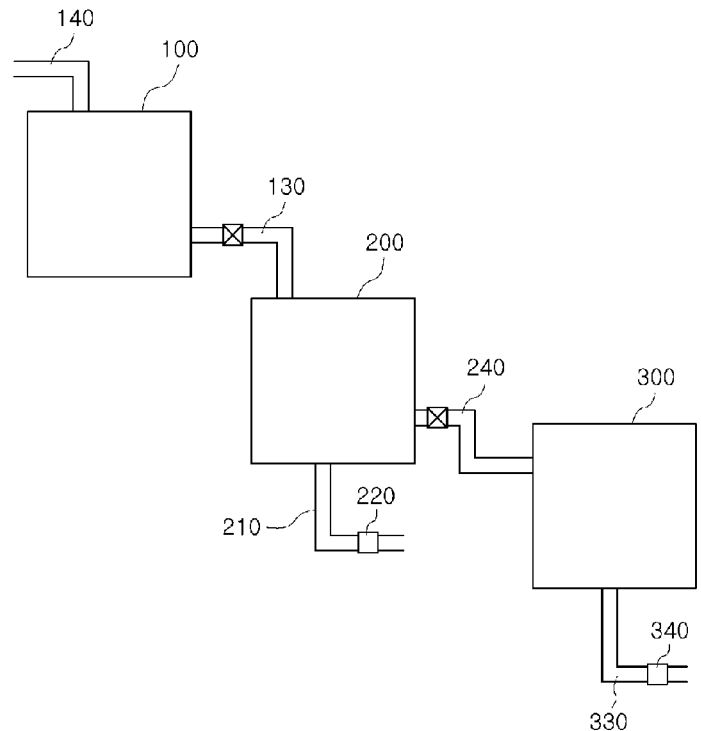
FIG. 7 is a schematic diagram illustrating a configuration of a water treatment apparatus having a plurality of tanks, to which a sterilizing method according to another exemplary embodiment of the present invention is applied.

FIG. 7 is a schematic diagram illustrating a configuration of a water treatment apparatus having a plurality of tanks, to which a sterilizing method according to another exemplary embodiment of the present invention is applied.

A first tank 100 may store purified water having passed through a filtration unit, and selectively drain the purified water. The first tank 100 may store sterilized water which flows in from a sterilizing module.

A second tank 200 may receive purified water from the first tank 100, make cold water, and store the cold water. That is, the second tank 200 may make cold water by cooling normal-temperature purified water using a cooler, and store the cold water.

The intermediate device 300 processes cold water supplied from the second tank 200. Specifically, the intermediate device 300 may be a third tank configured to store the cold water supplied from the first tank 200 and heat or cool the stored cold water, an ice maker configured to make ice by cooling the supplied cold water, or a carbonated water maker configured to make carbonated water by supplying carbon dioxide to the cold water. In addition, the intermediate device 300 may be a syrup addition device configured to add syrup or scent to the cold water.

Hereinafter, a water treatment apparatus including an ice maker as an example of the intermediate devices 300 will be described.

The ice maker 300 may receive cold water from the second tank 200 and make ice. The ice maker 300 may employ various ice making methods, for example, an ice making method using an ice tray and an immersion evaporator, or an injection type ice making method that makes ice by injecting water into a cooling container.

The first tank 100 may be supplied with purified water or sterilized water through a water inlet pipe 140. Although not illustrated, sterilized water generated by an electrolytic sterilizer may be supplied through the water inlet pipe 140 in a sterilizing mode.

In addition, the first tank 100 may include a second water outlet pipe 130 and a water intake pipe (not illustrated).

The second outlet pipe 130 may transfer water stored in the first tank 100 to the second tank 200. The second water outlet pipe 130 may include a valve for controlling water flow. If necessary, water flow may be controlled using a water jet pump.

The water intake pipe may drain water stored in the first tank 100 to the outside. In particular, the water intake pipe may be connected to a purified water cock and transfer purified water to a user. In addition, if necessary, the water intake pipe may include a valve for controlling the supply of purified water.

The ice maker 300 may further include a flow passage 330 that can discharge supplied cold water, without storing the supplied cold water in an ice tray. An intermediate device other than the ice maker 300 may also further include a flow passage 330 that can discharge supplied cold water, without storing the supplied cold water.

The second tank 200 may include a drain line 210, a drain valve (not illustrated), a drain pump 220, a third water outlet pipe 240, and a water intake pipe (not illustrated).

The drain line 210 is configured to drain water or sterilized water, stored in the second tank 200, as live water. The drain line 210 is provided as a drain pipe conduit connected to a bottom of the second tank 200.

The drain valve may control the opening/closing of the drain line 210, and the drain pump 220 may be installed in the drain line 210. The drain pump 220 is used to more effectively drain water stored in the second tank 200. Even in the case that the drain valve is opened, water is not drained rapidly if a cross-section of the drain line 210 is narrow. Since water is not drained completely, old purified water or sterilized water used in a sterilizing process may remain in the second tank 200.

The third water outlet pipe 240 may transfer water stored in the second tank 200 to the ice maker 300. The third water outlet pipe 240 may include a valve for controlling water flow. If necessary, water flow may be controlled using a water jet pump.

Although not illustrated, an electrolytic sterilizer may be installed in the water inlet pipe 140. The electrolytic sterilizer may be configured to generate sterilized water, including a sterilizing material such as a mixed oxidant (MO), through electrolysis using only purified water filtered by at least a part of filters provided in the filtration unit.

In addition, although not illustrated, a chemical sterilizer may be installed in the water inlet pipe 140. The chemical sterilizer may be configured to generate sterilized water, including a sterilizing material, using only purified water filtered by at least a part of filters provided in the filtration unit.

Furthermore, although not illustrated, a device configured to receive sterilized water from the outside may be installed in the water inlet pipe 140. The device may receive and store sterilized water prepared or generated in the outside, or may supply the sterilized water immediately to the water inlet pipe 140.

Figure 8:
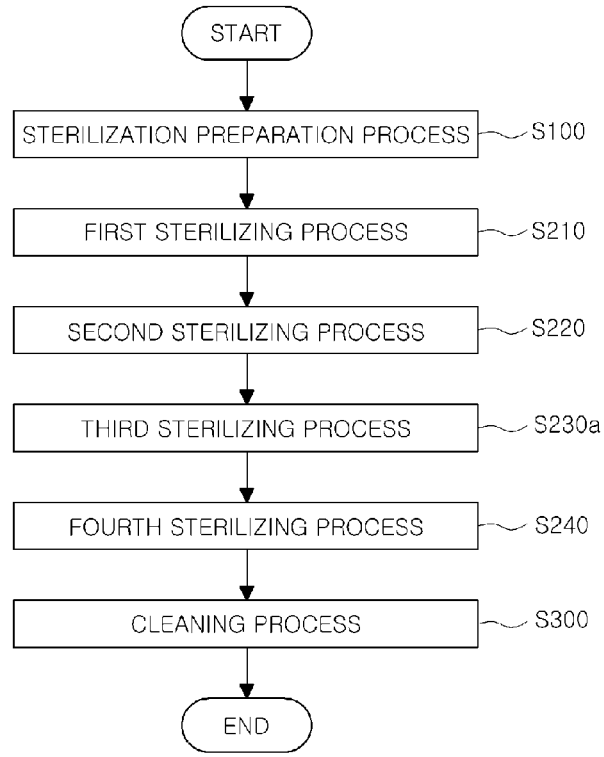
FIG. 8 is a flow diagram illustrating a method for sterilizing a water treatment apparatus having a plurality of tanks, according to another exemplary embodiment of the present invention.

FIG. 8 is a flow diagram illustrating a method for sterilizing a water treatment apparatus having a plurality of tanks, according to another exemplary embodiment of the present invention.

In a sterilization preparation process S100, purified water from the first tank 100 may be drained through the second water outlet pipe 130 until a first amount of purified water is left in the first tank 100. Purified water from the second tank 200, drained from the first tank 100, may be drained through the third water outlet pipe 240 until a second amount of purified water is left in the second tank 200. The first amount and the second amount may be determined, depending on a target dilution level of sterilized water being supplied at high concentration.

In a first sterilizing process S210, the first tank 100 may be sterilized by supplying sterilized water thereto. Water of the first tank 100 may be drained into the second tank 200 through the second water outlet pipe 130 until a third amount of water is left therein.

In a second sterilizing process S220, a fourth amount of sterilized water drained into the second tank 200 may be drained into the ice maker 300 through the third water outlet pipe 240. In particular, in the second sterilizing process S220, sterilized water may be drained from the second tank 200 during a fourth draining period, a period of time taken to drain the fourth amount of water from the second tank 200. An amount of drainage may be controlled by adjusting a draining period, without using a water level sensor or the like. The third water outlet pipe 240 may further include a flow rate sensor. In the second sterilizing process S220, the drainage of water from the second tank 200 may be stopped when the measured amount of drainage becomes equal to the fourth amount of water.

In a third sterilizing process S230a, sterilized water remaining in the first tank 100 may be drained into the second tank 200 through the second water outlet pipe 130.

In a fourth sterilizing process S240, sterilized water stored in the second tank 200 may be drained through the drain line 210.

Through the first to fourth sterilizing processes S210 to S240, the second water outlet pipe 130 and the third water outlet pipe 240, as well as the first tank 100 and the second tank 200, may be sterilized.

In a cleaning process S300, the first tank 100 may be cleaned by supplying purified water thereto. The purified water used to clean the first tank 100 may be drained into the second tank 200, and the second tank 200 may be cleaned with the purified water drained thereinto. Furthermore, a part of the purified water used to clean the second tank 200 may be drained into the ice maker 300, and washing water remaining in the second tank 200 may be drained through the drain line 210. Even in the case that the sterilized water is drained, the sterilized water may remain in several places in the first tank 100 and the second tank 200. In this case, the remaining sterilized water may be washed out by the purified water. In addition, the second water outlet pipe 130 and the third water outlet pipe 240 also may be cleaned.

Furthermore, when the cleaning process is completed, purified water may be supplied to the first tank 100 so as to allow a user to drink water. This may be done after or during the draining of the purified water used to clean the second tank 200.

As described above, the method for sterilizing the water treatment apparatus may sterilize and clean the plurality of tanks and flow passages.

Figure 9:
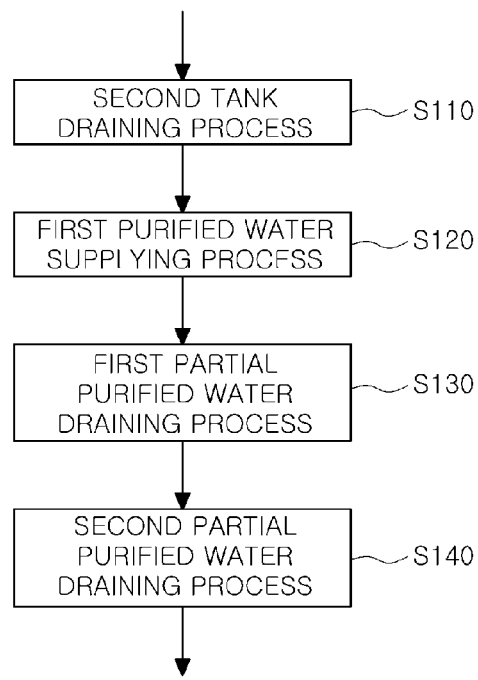
FIG. 9 is a flow diagram illustrating a detailed flow of a sterilization preparation process in the method for sterilizing the water treatment apparatus having a plurality of tanks, according to another exemplary embodiment of the present invention.

FIG. 9 is a flow diagram illustrating a detailed flow of the sterilization preparation process in the method for sterilizing the water treatment apparatus having a plurality of tanks, according to another exemplary embodiment of the present invention;

In a second tank draining process S110, cold water remaining in the second tank 200 may be drained. When cold water remains in the second tank 200, a desired amount of purified water may not be drained from the first tank 100. Therefore, it is necessary to completely drain water from the second tank 200.

In a first purified water supplying process S120, a preset volume of purified water may be supplied to the first tank 100. However, as described above, an amount of purified water remaining in the first tank 100 is difficult to measure unless an amount of purified water supplied or used is continuously tracked. An amount of purified water remaining in the first tank 100 may be exactly determined by setting the preset volume as a maximum storage amount of the first tank 100 and fully filling the first tank 100 with purified water.

In a first partial purified water draining process S130, purified water from the first tank 100 may be drained into the second tank 200 during a first draining period. The first draining period may be a period of time taken until an amount of water corresponding to a difference between the preset volume and the first amount of water is drained from the first tank 100 to the second tank 200. When the preset volume is a maximum storage amount of the first tank 100, the first draining period may be a period of time taken until an amount of water corresponding to a difference between the maximum storage amount of the first tank 100 and the first amount of water is drained from the first tank 100 to the second tank 200. The first draining period may be determined by the maximum storage amount of the first tank 100, the first amount of water, an amount of water drained per unit time from the second water outlet pipe 130, or the like, and may be previously determined in designing the water treatment apparatus. Therefore, the first draining period may be calculated theoretically or experimentally in designing the water treatment apparatus. That is, in the first partial purified water draining process S130, purified water may be drained during the first draining period of time determined using an estimated amount of the remaining purified water (full water level through the supply of purified water), a drainage rate, and the first amount of water.

In a second partial purified water draining process S140, the purified water drained from the first tank 100 may be drained during a second draining period, such that the second tank 200 is ready to store water drained from the first tank 100. A concentration of sterilized water used to sterilize the second tank 200 may be adjusted. The second draining period is a period of time taken to drain an amount of water corresponding to a result of a subtraction of the first amount of water and the second amount of water from the set volume.

As described above, instead of setting the first draining period and the second draining period, an amount of drainage may be directly measured using a flowmeter. That is, an amount of water drained from the first tank 100 and an amount of water drained from the second tank 200 are directly measured using the flowmeter, and the drainage of water may be stopped when the preset amount of water has been drained.

Figure 10:
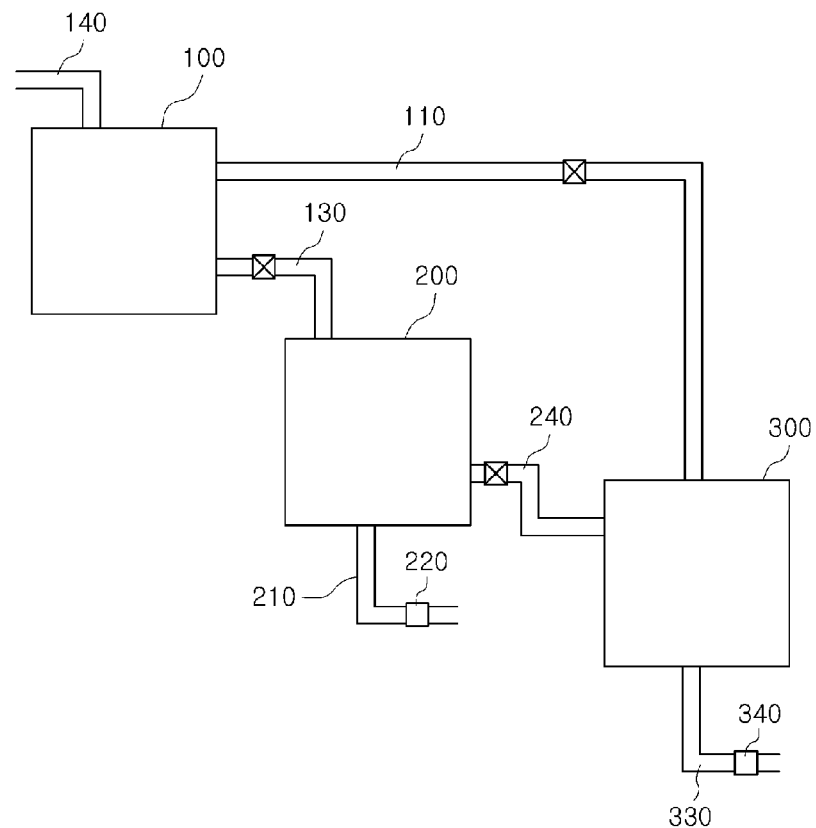
FIG. 10 is a schematic diagram illustrating a configuration of a water treatment apparatus having a plurality of tanks, to which a sterilizing method according to another exemplary embodiment of the present invention is applied.

FIG. 10 is a schematic diagram illustrating a configuration of a water treatment apparatus having a plurality of tanks, to which a sterilizing method according to another exemplary embodiment of the present invention is applied.

A first tank 100 may store purified water having passed through a filtration unit, and selectively drain the purified water. The first tank 100 may store sterilized water which flows in from a sterilizing module.

A second tank 200 may receive purified water from the first tank 100, make cold water, and store the cold water. That is, the second tank 200 may make cold water by cooling normal-temperature purified water using a cooler, and store the cold water.

An intermediate device 300 processes purified water supplied from the first tank 100. Specifically, the intermediate device 300 may be a third tank configured to store the purified water supplied from the first tank 100 and heat or cool the stored purified water, an ice maker configured to make ice by cooling the supplied purified water, or a carbonated water maker configured to make carbonated water by supplying carbon dioxide to the purified water. In addition, the intermediate device 300 may be a syrup addition device configured to add syrup or scent to the purified water.

Hereinafter, a water treatment apparatus including an ice maker as an example of the intermediate devices 300 will be described. However, the intermediate device 300 according to an exemplary embodiment of the present invention is not limited to the ice maker. Examples of the intermediate device 300 may include various types of devices, including the third tank, the carbonated water maker, and the syrup addition device.

The ice maker 300 may be supplied with purified water from the first tank 100 or cold water from the second tank 200, and make ice of the supplied purified water or cold water. The ice maker 300 may employ various ice making methods, for example, an ice making method using an ice tray and an immersion evaporator, or an injection type ice making method that makes ice by injecting water into a cooling container.

The first tank 100 may be supplied with purified water or sterilized water through a water inlet pipe 140. Although not illustrated, sterilized water generated by an electrolytic sterilizer may be supplied through the water inlet pipe 140 in a sterilizing mode.

In addition, the first tank 100 may include a first water outlet pipe 110, a second water outlet pipe 130, and a water intake pipe (not illustrated).

The first water outlet pipe 110 may transfer water stored in the first tank 100 to the ice maker 300. The first water outlet pipe 110 may include a valve for controlling water flow. If necessary, the first water outlet pipe 110 may control water flow using a water jet pump.

The second outlet pipe 130 may transfer water stored in the first tank 100 to the second tank 200. The second water outlet pipe 130 may include a valve for controlling water flow. If necessary, water flow may be controlled using a water jet pump.

The water intake pipe may drain water stored in the first tank 100 to the outside. In particular, the water intake pipe may be connected to a purified water cock and transfer purified water to a user. In addition, if necessary, the water intake pipe may include a valve for controlling the supply of purified water.

As illustrated in FIG. 2, the first water outlet pipe 110, the water intake pipe, and the second water outlet pipe 130 may be installed on the side of the first tank 100 in order from top to bottom. Therefore, sterilized water flowing into the first tank 100 may be drained into the ice maker 300 through the first water outlet pipe 110, and then, the sterilized water may be drained into the second tank 200 through the second water outlet pipe 130. Therefore, as described above, the inflow of sterilized water into the water intake pipe may be minimized.

The ice maker 300 may further include a flow passage 330 which can discharge the supplied purified water or cold water, without storing the supplied purified water or cold water in an ice tray. An intermediate device other than the ice maker 300 may also further include a flow passage 330 that can discharge the supplied cold water, without storing the supplied cold water.

The second tank 200 may include a drain line 210, a drain valve (not illustrated), a drain pump 220, a third water outlet pipe 240, and a water intake pipe (not illustrated).

The drain line 210 is configured to drain water or sterilized water, stored in the second tank 200, as live water. The drain line 210 is provided as a drain pipe conduit connected to a bottom of the second tank 200.

The drain valve may control the opening/closing of the drain line 210, and the drain pump 220 may be installed in the drain line 210. The drain pump 220 is used to more effectively drain water stored in the second tank 200. Even in the case that the drain valve is opened, water is not drained rapidly if a cross-section of the drain line 210 is narrow. Since water is not drained completely, old purified water or sterilized water used in a sterilizing process may remain in the second tank 200.

The third water outlet pipe 240 may transfer water stored in the second tank 200 to the ice maker 300. The third water outlet pipe 240 may include a valve for controlling water flow. If necessary, water flow may be controlled using a water jet pump.

Figure 11:
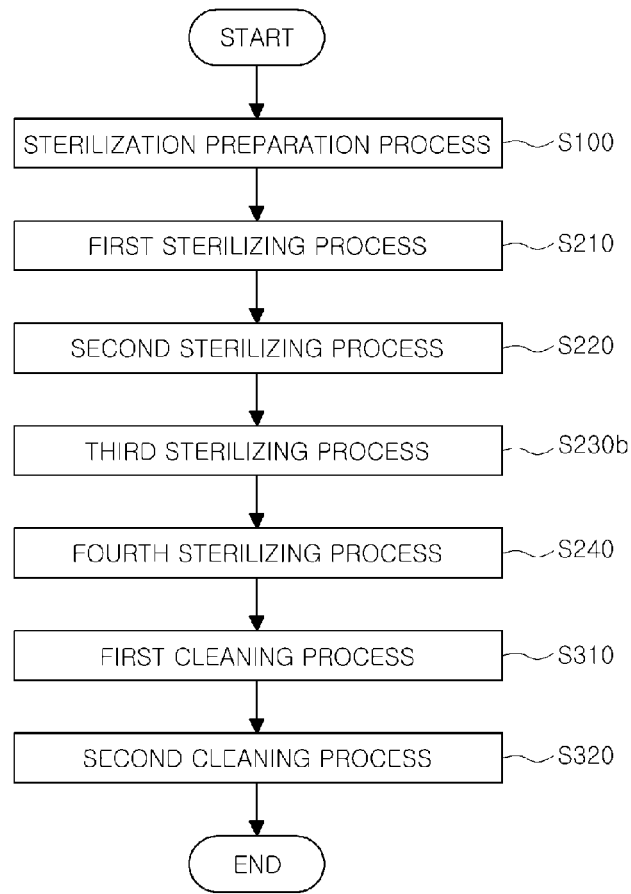
FIG. 11 is a flow diagram illustrating a method for sterilizing a water treatment apparatus having a plurality of tanks, according to another exemplary embodiment of the present invention.

FIG. 11 is a flow diagram illustrating a method for sterilizing a water treatment apparatus having a plurality of tanks, according to another exemplary embodiment of the present invention.

In a sterilization preparation process S100, purified water from the first tank 100 may be drained through the second water outlet pipe 130 until a first amount of purified water is left in the first tank 100. Purified water from the second tank 200, drained from the first tank 100, may be drained through the third water outlet pipe 240 until a second amount of purified water is left in the second tank 200. The first amount and the second amount may be determined, depending on a target dilution level of sterilized water being supplied at high concentration.

In a first sterilizing process S210, the first tank 100 may be sterilized by supplying sterilized water thereto. Water of the first tank 100 may be drained into the second tank 200 through the second water outlet pipe 130 until a third amount of water is left therein. That is, after the first tank 100 is sterilized by supplying sterilized water thereto, sterilized water may be divided and drained.

In a second sterilizing process S220, a fourth amount of sterilized water drained into the second tank 200 may be drained into the ice maker 300 through the third water outlet pipe 240. In particular, in the second sterilizing process S220, sterilized water may be drained from the second tank 200 during a fourth draining period. The fourth draining period is a period of time taken to drain the fourth amount of water from the second tank 200. An amount of drainage may be controlled by adjusting a draining period of time, without using a water level sensor or the like. The third water outlet pipe 240 may further include a flow rate sensor. In the second sterilizing process S220, the drainage of water from the second tank 200 may be stopped when the measured amount of drainage becomes equal to the fourth amount of water.

In a third sterilizing process S230*b*, sterilized water remaining in the first tank 100 may be drained into the ice maker 300 through the first water outlet pipe 110.

In a fourth sterilizing process S240, sterilized water stored in the second tank 200 may be drained through the drain line 210.

Through the first to fourth sterilizing processes S210 to S240, the first water outlet pipe 110, the second water outlet pipe 130, and the third water outlet pipe 240, as well as the first tank 100 and the second tank 200, may be sterilized.

The first to fourth sterilizing processes S210 to S240 may not be sequentially performed. That is, the third sterilizing process S230*b* may be performed after the first sterilizing process S210. Alternatively, the first sterilizing process S210 and the second sterilizing process S220 may be performed after the third sterilizing process S230*b*.

Specifically, in the first sterilizing process S210, sterilized water of the first tank 100 is drained into the second tank 200 until a third amount of sterilized water is left therein. Then, in the third sterilizing process S230*b*, the second amount of water remaining in the first tank 100 may be drained into the ice maker 300. Then, a fourth amount of sterilized water drained into the second tank 200 in the second sterilizing process S220 may be drained into the ice maker 300.

In addition, the first tank 100 may be sterilized by supplying sterilized water supplied from the sterilizing module to the first tank 100. Then, as opposed to the first sterilizing process S210, the sterilized water may be drained not into the second tank 200 but into the ice maker 300. Sterilized water of the first tank 100 may be drained into the ice maker 300 until a third amount of water is left in the first tank 100. Then, a second amount of sterilized water remaining in the first tank 100 may be drained into the second tank 200. Finally, a fourth amount of sterilized water drained from the second tank 200 may be drained into the ice maker 300. In this manner, the sterilizing process may be finished.

That is, the first to fourth sterilizing processes S210 to S240 may be performed in various orders as long as the processes can sterilize the first tank 100, the second tank 200, and the ice maker 300.

In a first cleaning process S310, the first tank 100 may be cleaned by supplying purified water thereto. Some of the purified water used to clean the first tank 100 may be drained into the ice maker 300, and the rest of the purified water may be drained into the second tank 200.

In a second cleaning process S320, some of the purified water used to clean the second tank 200 may be drained into the ice maker 300, and washing water remaining in the second tank 200 may be drained through the drain line 210.

Even in the case that the sterilized water is drained, the sterilized water may remain in several places in the first tank 100 and the second tank 200. In this case, the remaining sterilized water may be washed out by the purified water. In addition, the first water outlet pipe 110, the second water outlet pipe 130, and the third water outlet pipe 240 may be cleaned.

Furthermore, when the cleaning process is completed, a preset volume of purified water may be supplied to the first tank 100 so as to allow a user to drink water. This may be done after or during the draining of the purified water used to clean the second tank 200.

As described above, the method for sterilizing the water treatment apparatus may sterilize and clean the plurality of tanks and flow passages.

A detailed flow of the sterilization preparation process S100 will be described below with reference to FIG. 9. Since it is enough to adjust the first amount and the second amount between the first tank 100 and the second tank 200, the sterilization preparation process S100 illustrated in FIG. 9 may be applied.

In the second tank draining process S110, cold water remaining in the second tank 200 may be drained. When cold water remains in the second tank 200, a desired amount of purified water may not be drained from the first tank 100. Therefore, it is necessary to completely drain water from the second tank 200.

In the first purified water supplying process S120, a preset volume of purified water may be supplied to the first tank 100. However, as described above, an amount of purified water remaining in the first tank 100 is difficult to measure unless an amount of purified water supplied or used is continuously tracked. An amount of purified water remaining in the first tank 100 may be exactly determined by setting the preset volume as a maximum storage amount of the first tank 100 and fully filling the first tank 100 with purified water.

In addition, in the first partial purified water draining process S130, purified water from the first tank 100 may be drained into the second tank 200 during a first draining period. The first draining period may be a period of time taken until an amount of water corresponding to a difference between the preset volume and the first amount of water is drained from the first tank 100 to the second tank 200.

In the second partial purified water draining process S140, the purified water drained from the first tank 100 may be drained during a second draining period, such that the second tank 200 is ready to store water drained from the first tank 100. A concentration of sterilized water used to sterilize the second tank 200 may be adjusted. The second draining period is a period of time taken to drain an amount of water corresponding to a result of a subtraction of the first amount of water and the second amount of water from the set volume of the first tank 100.

As described above, instead of setting the first draining period and the second draining period, an amount of drainage may be directly measured using a flowmeter. That is, an amount of water drained from the first tank 100 and an amount of water drained from the second tank 200 are directly measured using the flowmeter, and the drainage of water may be stopped when the preset amount of water has been drained.

In the first to fourth sterilizing processes S210 to S240, sterilized water may be drained through the respective flow passages, such that the first water outlet pipe 110, the second water outlet pipe 130, and the third water outlet pipe 240, as well as the first tank 100 and the second tank 200, are sterilized.

In addition, in the first cleaning process S310 and the second cleaning process S320, washing water may be drained through the respective flow passages, such that the first water outlet pipe 110, the second water outlet pipe 130, and the third water outlet pipe 240, as well as the first tank 100 and the second tank 200, are cleaned.

Figure 12:
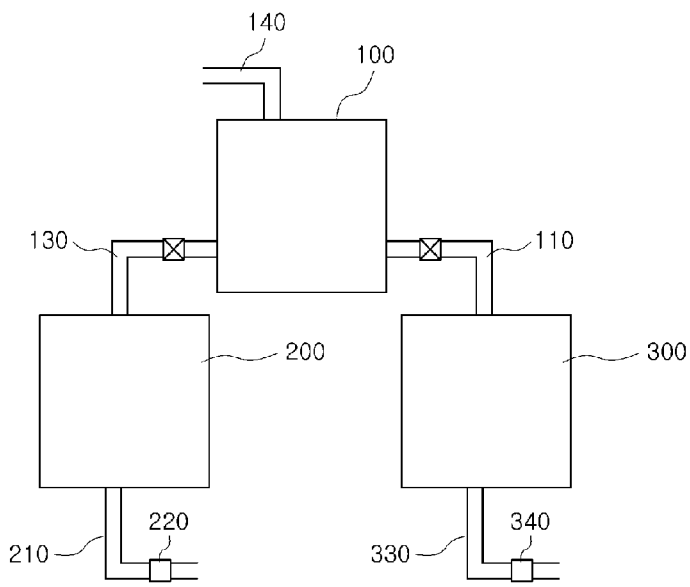
FIG. 12 is a schematic diagram illustrating a configuration of a water treatment apparatus having a plurality of tanks, to which a sterilizing method according to another exemplary embodiment of the present invention is applied.

FIG. 12 is a schematic diagram illustrating a configuration of a water treatment apparatus having a plurality of tanks, to which a sterilizing method according to another exemplary embodiment of the present invention is applied.

A first tank 100 stores purified water having passed through a filtration unit and selectively drains the purified water. The first tank 100 may store sterilized water which flows in from a sterilizing module.

A second tank 200 may receive purified water from the first tank 100, make cold water, and store the cold water. That is, the second tank 200 may make cold water by cooling normal-temperature purified water using a cooler, and store the cold water.

The intermediate device 300 processes purified water supplied from the second tank 100. Specifically, the intermediate device 300 may be a third tank configured to store the purified water supplied from the first tank 100 and heat or cool the stored purified water, an ice maker configured to make ice by cooling the supplied purified water, or a carbonated water maker configured to make carbonated water by supplying carbon dioxide to the purified water. In addition, the intermediate device 300 may be a syrup addition device configured to add syrup or scent to the purified water.

Hereinafter, a water treatment apparatus including an ice maker as an example of the intermediate devices 300 will be described. However, the intermediate device 300 according to an exemplary embodiment of the present invention is not limited to the ice maker. Examples of the intermediate device 300 may include various types of devices, including the third tank, the carbonated water maker, and the syrup addition device.

The ice maker 300 may make ice of purified water supplied from the first tank 100. The ice maker 300 may employ various ice making methods, for example, an ice making method using an ice tray and an immersion evaporator, or an injection type ice making method that makes ice by injecting water into a cooling container.

The first tank 100 may be supplied with purified water or sterilized water through a water inlet pipe 140. Although not illustrated, sterilized water generated by an electrolytic sterilizer may be supplied through the water inlet pipe 140 in a sterilizing mode.

In addition, the first tank 100 may include a first water outlet pipe 110, a second water outlet pipe 130, and a water intake pipe (not illustrated).

The first water outlet pipe 110 may transfer water stored in the first tank 100 to the ice maker 300. The first water outlet pipe 110 may include a valve for controlling water flow. If necessary, water flow may be controlled using a water jet pump.

The second outlet pipe 130 may transfer water stored in the first tank 100 to the second tank 200. The second water outlet pipe 130 may include a valve for controlling water flow. If necessary, water flow may be controlled using a water jet pump.

The water intake pipe may drain water stored in the first tank 100 to the outside. In particular, the water intake pipe may be connected to a purified water cock and transfer purified water to a user. In addition, if necessary, the water intake pipe may include a valve for controlling the supply of purified water.

As illustrated in FIG. 2, the first water outlet pipe 110, the water intake pipe, and the second water outlet pipe 130 may be installed on the side of the first tank 100 in order from top to bottom. Therefore, sterilized water flowing into the first tank 100 may be drained into the ice maker 300 through the first water outlet pipe 110, and then, the sterilized water may be drained into the second tank 200 through the second water outlet pipe 130. That is, as described above, the inflow of sterilized water into the water intake pipe may be minimized.

The ice maker 300 may further include a flow passage 330 which can discharge the supplied purified water or cold water, without storing the supplied purified water or cold water in an ice tray. An intermediate device other than the ice maker 300 may further include a flow passage 330 which can discharge the supplied cold water, without storing the supplied cold water. A drain pump 340 may be further included so as to increase a drainage rate.

The second tank 200 may include a drain line 210, a drain valve (not illustrated), a drain pump 220, and a water intake pipe (not illustrated).

The drain line 210 is configured to drain water or sterilized water, stored in the second tank 200, as live water. The drain line 210 is provided as a drain pipe conduit connected to a bottom of the second tank 200.

The drain valve may control the opening/closing of the drain line 210, and the drain pump 220 may be installed in the drain line 210. The drain pump 220 is used to more effectively drain water stored in the second tank 200. Even in the case that the drain valve is opened, water is not drained rapidly if a cross-section of the drain line 210 is narrow. Since water is not drained completely, old purified water or sterilized water used in a sterilizing process may remain in the second tank 200.

A method for sterilizing a water treatment apparatus having a plurality of tanks, according to another exemplary embodiment of the present invention, will be described with reference to FIG. 3.

In a sterilization preparation process S10, purified water from the first tank 100 may be drained through the second water outlet pipe 130 until a first amount of purified water is left in the first tank 100. The first amount may be determined, depending on a target dilution level of high-concentration sterilized water.

Hereinafter, the sterilization preparation process S10 will be described in detail.

First, cold water remaining in the second tank 200 may be drained. When cold water remains in the second tank 200, a desired amount of purified water may not be drained from the first tank 100. Therefore, it is necessary to completely drain water from the second tank 200.

Then, a preset volume of purified water may be supplied to the first tank 100. However, an amount of purified water remaining in the first tank 100 is difficult to measure unless an amount of purified water supplied or used is continuously tracked. Therefore, an amount of purified water remaining in the first tank 100 may be exactly determined by setting the preset volume as a maximum storage amount of the first tank 100 and fully filling the first tank 100 with purified water.

Purified water from the first tank 100 may be drained into the second tank 200 during a first draining period. The first draining period may be a period of time taken until an amount of water corresponding to a difference between the preset volume and the first amount of water is drained from the first tank 100 to the second tank 200. An amount of water drained from the first tank 100 to the second tank 200 may be adjusted using a flowmeter. That is, an amount of water corresponding to a difference between the preset volume and the first amount of water may be drained using the flowmeter.

In a sterilizing process S20, the first tank 100 may be sterilized by supplying sterilized water thereto. Water from the first tank 100 may be drained into the second tank 200 through the second water outlet pipe 130 until a second amount of water is left therein. The remaining water may be drained into the ice maker 300 through the first water outlet pipe 110. That is, after the first tank 100 is sterilized by supplying sterilized water thereto, the sterilized water may be divided and drained into the second tank 200 and the ice maker 300.

Specifically, the first tank 100 may be sterilized by supplying sterilized water thereto, and the sterilized water may be drained into the second tank 200 during a second draining period. The second draining period may be a period of time taken to drain an amount of water corresponding to a difference between the preset volume and the second amount of water. In the sterilizing process S20, the second amount of water may be controlled by adjusting a draining period, without using a water level sensor or the like. After draining the sterilized water into the second tank 200, the remaining sterilized water may be drained into the ice maker 300.

Instead of setting the second draining period, an amount of water drained may be directly measured using a flowmeter. That is, an amount of water drained from the first tank 100 is directly measured using the flowmeter, and the drainage of water is stopped when an amount of water corresponding to a difference between the preset volume and the second amount of water has been drained.

Through the sterilizing process S20, the first water outlet pipe 110 and the second water outlet pipe 130, as well as the first tank 100 and the second tank 200, may be sterilized.

In a cleaning process 30, the first tank 100 may be cleaned by supplying purified water thereto. Some of the purified water used to clean the first tank 100 may be drained into the second tank 200, and the rest of the purified water may be drained into the ice maker 300. Washing water remaining in the second tank 200 may be drained through the drain line 210.

Even in the case that the sterilized water is drained, the sterilized water may remain in several places in the first tank 100 and the second tank 200. In this case, the remaining sterilized water may be washed out by the purified water. In addition, the first water outlet pipe 110 and the second water outlet pipe 130 may be cleaned.

Furthermore, when the cleaning process is completed, a preset volume of purified water may be supplied to the first tank 100 so as to allow a user to drink water. This may be done after or during the draining of the purified water used to clean the second tank 200.

As described above, the method for sterilizing the water treatment apparatus may sterilize and clean the plurality of tanks and flow passages.

While the present invention has been shown and described in connection with the exemplary embodiments, it will be apparent to those skilled in the art that modifications and variations can be made without departing from the spirit and scope of the invention as defined by the appended claims.

The invention claimed is:

1. A method for sterilizing a water treatment apparatus including a sterilizing module, which generates or receives sterilized water and supplies the sterilized water, a first tank, and a second tank, the method comprising:
   performing a sterilization preparation process to drain purified water from the first tank until a first amount of purified water is left in the first tank;
   performing a sterilizing process to sterilize the first tank by supplying the sterilized water supplied from the sterilizing module to the first tank, to drain water from the first tank through a first water outlet pipe until a second amount of water is left in the first tank, and to drain the second amount of water remaining in the first tank into the second tank through a second water outlet pipe; and
   performing a cleaning process to clean the first tank by supplying purified water to the first tank, and to drain the purified water used to clean the first tank into the second tank.

2. The method of claim 1, wherein in the sterilizing process, water of the first tank is drained into the second tank through the second water outlet pipe until a second amount of water is left in the first tank, and the second amount of water remaining in the first tank is drained through the first water outlet pipe.

3. The method of claim 1, wherein the first water outlet pipe is configured to supply water to an intermediate device included in the water treatment apparatus, and the intermediate device is connected to the second tank and configured to bypass water supplied from the first water outlet pipe to the second tank.

4. The method of claim 3, wherein the intermediate device is any one of a third tank, an ice maker, a carbonated water maker, and a syrup addition device.

5. The method of claim 1, wherein the sterilization preparation process comprises:
   supplying a preset volume of purified water to the first tank; and draining the purified water stored in the first tank during a first draining period, the first draining period being a period of time taken to drain an amount of water corresponding to a difference between the preset volume and the first amount of water.

6. The method of claim 1, wherein the sterilizing process comprises:
   sterilizing the first tank by supplying a preset volume of the sterilized water supplied from the sterilizing module to the first tank;
   draining the sterilized water stored in the first tank through the first water outlet pipe during a second draining period; and
   draining the water remaining in the first tank through the second water outlet pipe, the second draining period being a period of time taken to drain an amount of water corresponding to a difference between the preset volume and the second amount of water.

7. The method of claim 2, wherein the sterilizing process comprises:
   sterilizing the first tank by supplying a preset volume of the sterilized water supplied from the sterilizing module to the first tank;
   draining the sterilized water stored in the first tank through the second water outlet pipe during a draining period; and
   draining the water remaining in the first tank through the first water outlet pipe, the draining period being a period of time taken to drain an amount of water corresponding to a difference between the preset volume and the second amount of water.

8. The method of claim 6, further comprising draining sterilized water stored in the second tank after the sterilizing process.

9. The method of claim 1, wherein the cleaning process comprises:
   cleaning the first tank by supplying a preset volume of purified water to the first tank;
   draining the supplied purified water stored in the first tank into the second tank; and
   draining the purified water drained into the second tank.

10. The method of claim 9, wherein the purified water is supplied to the first tank at the same time as the draining of the purified water drained into the second tank, or the purified water is supplied to the first tank after the draining of the purified water drained into the second tank.

11. The method of claim 1, wherein the water treatment apparatus includes the first water outlet pipe, the second water outlet pipe, and a water intake pipe, which are installed on a side of the first tank, the water intake pipe is configured to supply water stored in the first tank to a user, the first water outlet pipe is disposed above the water intake pipe, and the second water outlet pipe is disposed under the water intake pipe.

12. The method of claim 11, wherein the water treatment apparatus further includes:
   a drain line configured to drain water stored in the second tank;
   a drain valve configured to open/close the drain line; and
   a drain pump installed in the drain line.

13. The method of claim 11, wherein when the second amount of water is stored in the first tank, a height of a water surface falls to within a range between a height of the water intake pipe and a height of the first water outlet pipe.

14. The method of claim 1, wherein the first amount of water is determined, depending on a target dilution level of the sterilized water.

15. The method of claim 1, wherein the sterilizing module generates the sterilized water by using one of an electrolytic sterilizer employing electrolysis and a chemical sterilizer employing sterilizing chemicals.

* * * * *